United States Patent [19]

Wenzel et al.

[11] Patent Number: 5,067,085
[45] Date of Patent: Nov. 19, 1991

[54] OPTICAL ROBOTIC CANOPY POLISHING SYSTEM

[75] Inventors: Dennis J. Wenzel; David S. McFalls, II, both of San Antonio, Tex.

[73] Assignee: Southwest Research Institute, San Antonio, Tex.

[21] Appl. No.: 352,600

[22] Filed: May 15, 1989

[51] Int. Cl.$^5$ .............................................. G06F 15/46
[52] U.S. Cl. ............................ 364/474.06; 51/165.71; 51/165.72; 364/507; 901/41; 901/44; 901/47; 395/94
[58] Field of Search ....................... 364/474.06, 474.05, 364/474.37, 513, 507; 51/165.71, 165.72; 358/101, 106, 107; 901/41, 44, 47; 250/562, 563, 571, 572; 356/237

[56] References Cited

U.S. PATENT DOCUMENTS

| | | | |
|---|---|---|---|
| 4,355,447 | 10/1982 | DiMatteo et al. | 364/474.05 |
| 4,409,718 | 10/1983 | Pryor | 364/476 X |
| 4,541,011 | 9/1985 | Mayer et al. | 356/237 X |
| 4,633,620 | 1/1987 | Lorenzi et al. | 51/165.72 X |
| 4,682,856 | 7/1987 | Holdridge | 351/159 |
| 4,777,769 | 10/1988 | McLaughlin et al. | 51/165.72 X |

Primary Examiner—Joseph Ruggiero
Attorney, Agent, or Firm—Pravel, Gambrell, Hewitt, Kimball & Krieger

[57] ABSTRACT

A method and apparatus for providing an automated optical robotic polishing system for removing flaws in transparencies, such as transparent canopies used in aircraft. A pneumatic random orbital polishing tool attached to a robot arm is used to polish canopies to remove flaws. The flaws are removed by grinding the area surrounding the flaw and smoothing the flaw site to conform to the contour of the canopy. To identify optimum motions for the polishing tool for grinding to remove the bulk of the plastic material around a flaw, mathematical topology simulation techniques are implemented using various polishing pad pressure profiles and various polishing motions.

11 Claims, 10 Drawing Sheets

OPTICAL ROBOTIC CANOPY POLISHING SYSTEM

FIELD OF THE INVENTION

The present invention relates generally to polishing systems for removing flaws from the surface of a material. More particularly, the present invention provides an improved method and apparatus for determining the location and severity of a flaw and for calculating an optimum grinding pattern for removing the flaw.

BACKGROUND

Aircraft canopy transparencies are subjected to harsh environments, leaving them scratched, pitted, and crazed. This damage adversely affects the vision of the pilot and weakens the canopy structure. Replacement of a damaged canopy is extremely expensive, especially in cases where the damaged portion of the canopy is a large structure. A less costly alternative to replacement of the canopy is to rework the transparency by polishing to improve optical characteristics and to relieve stress in areas prone to cracking.

Prior methods for reworking aircraft transparencies have involved manual techniques which are labor intensive and are not always successful. In such methods, canopies are typically brought into a work area where a human expert inspects the transparency visually. Some canopies are obvious rejects to the inspector, but others require a very close inspection to identify flaws that exceed a critical depth into the plastic or to locate stress crazing. Canopies which fail inspection require the costly replacement of the transparencies. Canopies passing the inspection are manually sanded and polished to correct the flaws. Sanding in the vicinity of a flaw must be done expertly to avoid improper removal of transparency material that would introduce unacceptable optical distortion or remove excessive material and to avoid overheating of the plastic which weakens and discolors it.

Because manual restoration methods require subjective decisions regarding the severity of flaws and manual polishing to correct the flaws, the results are often inconsistent. Furthermore, manual restoration techniques are time consuming and expensive. The prior art has heretofore lacked an automated system for polishing aircraft transparencies to remove flaws. The method and apparatus of the present invention, as discussed in greater detail below, fulfills this need by providing a cost effective automated process for polishing such transparencies to obtain high quality, repeatable results.

SUMMARY OF THE INVENTION

The method and apparatus of the present invention provides an automated optical robotic polishing system for removing flaws in transparencies, such as transparent canopies used in aircraft. In the system of the present invention, a pneumatic random orbital polishing tool attached to a robot arm is used to polish canopies to remove flaws. The flaws are removed by grinding the area surrounding the flaw and smoothing the flaw site to conform to the contour of the canopy. To identify optimum motions for the polishing tool for grinding to remove the bulk of the plastic material around a flaw, mathematical topology simulation techniques are implemented using various polishing pad pressure profiles and various polishing motions.

The system of the present invention operates in accordance with the following constraints: 1) to remove the flaws completely; 2) to minimize the number of grinding patterns laid on the transparency; and 3) to minimize the distortion caused by overlapping grinding patterns. The initial step in the method of the present invention requires identification of transparency locations that require rework. This is done by outlining the transparency flaws with white, water soluble paint, which is easily removed later through the polishing motion of the robot system. The processing steps include the following operations: 1) initial overall inspection 2) cleaning or polishing, 3) flaw gradation, 4) grinding site selection, 5) abrasive removal of canopy material, 6) intermittent in-process inspection to determine when flaws have been removed, 7) abrasive refinishing to clarity, and 8) overall polishing. The polishing is implemented in steps, with the first step employing a coarse grain paper and the final step employing a very fine grain paper, on the order of 15 microns.

DETAILED DESCRIPTION OF THE PREFERRED EMBODIMENT

Figure 1:
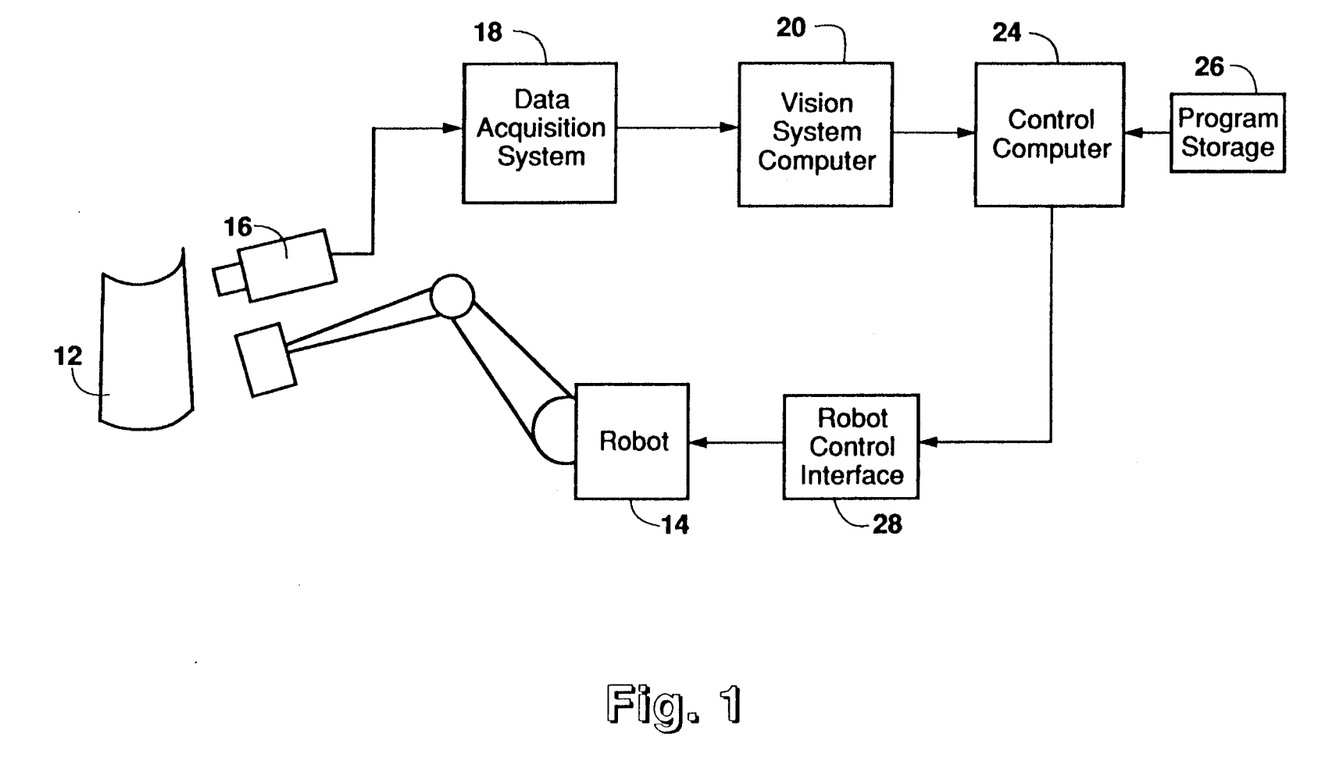
FIG. 1 is a system block diagram of the automated robotic canopy polishing system of the present invention.

Referring to FIG. 1, a schematic block diagram is shown of an automated robotic canopy polishing system in accordance with the present invention. An "end effector" or polishing mechanism 10 is shown positioned over the surface of a canopy 12 to be polished. In the preferred embodiment of the invention, a polishing pad (not shown) having a coarse grit sandpaper, such as 30 micron, is used initially to remove flaws, while finer grit sandpapers, such as 15 micron and 9 micron, are used in subsequent stages to reduce surface roughness induced by the coarser grit sanding and to restore clarity. Overall restoration of a smooth contour to the canopy surface is achieved by moving the polishing mechanism 10 through a path of points mapped onto the canopy surface, with the polishing mechanism 10 being normal to the surface. The position of the polishing mechanism is controlled by a robot 14. The method for determining the optimum grinding path will be discussed in greater detail below.

The processing steps implemented to refinish a transparency 12 include: initial overall inspection, cleaning or polishing, flaw gradation, grinding site selection, abrasive removal of canopy material, intermittent in-process inspection to determine when flaws have been removed, abrasive refinishing to restore clarity, and finally, overall polishing.

A strobe illuminated video camera 16 provides a video representation of the surface of the canopy. The output of the video camera 16 is connected to a data acquisition system 18 which is operable to convert the video signals from the video camera 16 into a voltage signal which can be transferred to a vision system computer 20. In the preferred embodiment of the invention, the vision system computer is an International Robomation/Intelligence Model D-256. The signals received by the vision system computer 20 are converted, using techniques known in the art, into data signals which can be used by control computer 24. The control computer uses an algorithm stored in program storage 26 to process the data signals to determine the optimum polishing pattern, to monitor the effectiveness of the polishing activities and to provide appropriate control signals to robot control interface 28. The robot 14 can thus be controlled to move the polishing mechanism 10 over the surface 12 in a manner to optimize the polishing process. Although the system illustrated in FIG. 1 is shown with a single robot 14, it is apparent that multiple robots could be used for the various polishing steps. In the preferred embodiment of the system, two or more robots are employed to perform the polishing activities.

The following discussion will be directed to the methodology employed to determine where best to remove plastic from the canopy given the raw data indicating flaw positions and severity. This method is optimized in accordance with the following requirements: 1) to completely remove the flaws, 2) to minimize the number of grinding patterns laid on the canopies, and 3) to minimize the distortion caused by overlapping grinding patterns.

CANOPY MAPPING

Figure 2:
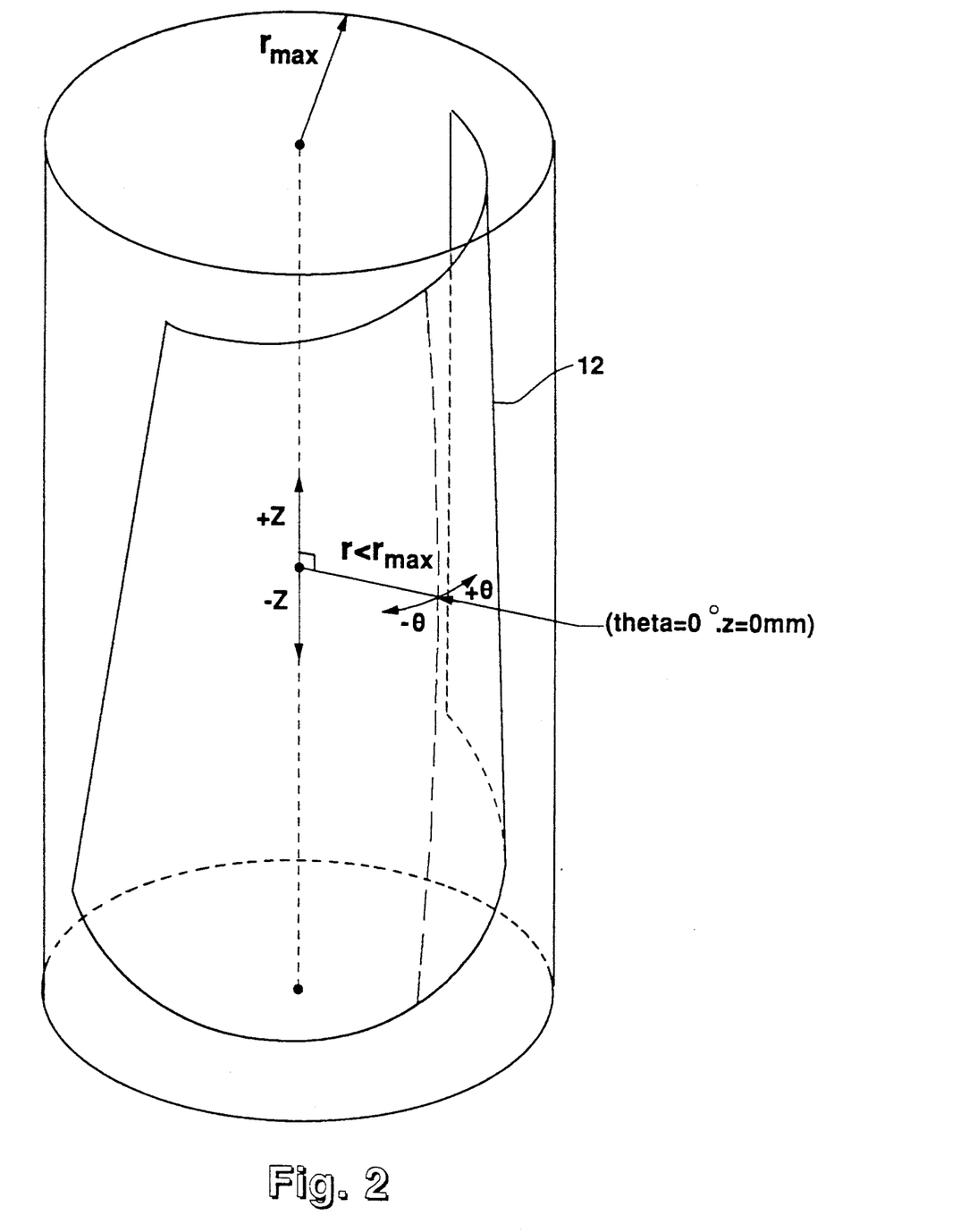
FIG. 2 is an illustration of a cylindrical coordinate system used to map the surface of an aircraft canopy in accordance with the method of the present invention.

As was discussed previously, restoration of a smooth contour to the surface of the canopy 12 is achieved by moving the polisher 10 through a path of points mapped onto the canopy surface, with the polisher 10 normal to the surface. This surface mapped path of points is called the grinding path. FIG. 2 is an illustration of a coordinate system used in the method of the present invention to obtain a map of the canopy surface. The model is used to project points from a given plane in three dimensions onto the surface of the canopy. These planar points may represent points along a path for grinding or points viewed by the inspection system.

The inside and outside surfaces of a canopy are modeled as composite surfaces constructed from overlapping bicubic patches. These patches are defined parametrically by an angle $\theta$ and a height $z$. The surface is bounded such that in parameter-space the angle $\theta$ must be between a minimum $\theta_{min}$ and a maximum $\theta_{max}$, and the height $z$ must be between a minimum $z_{min}$ and a maximum $z_{max}$. The size of each bicubic surface patch is determined by $n_\theta$ control points equally distributed in the $\theta$ parameter, and $n_z$ control points equally distributed in the $z$ parameter. For bicubic surface patches, the values of $n_\theta$ and $n_z$ must be larger than three. Due to this equal spacing of parameters $\theta$ and $z$, the sixteen-point form of a biparametric cubic surface is used. This technique is discussed in the following reference: M. E. Mortenson, *Geometric Modeling*, John Wiley & Sons, 1985.

Due to the surface curvature of the canopy, the surface is modeled by a composition of overlapping bicubic surface patches, where neighboring patches share common control points. To obtain a point on the surface of the canopy given the parameter values of $\theta$ and $z$, the bicubic surface patch where $\theta$ and $z$ are nearest the center of the patch, is selected. This method of constructing the composite surface guarantees $C^0$ continuity; i.e., there are no gaps or breaks between the beginning and ending points on any curve on this composite surface. This method of constructing the composite surface, however, fails to guarantee $C^1$ continuity, i.e., the tangent vector for a surface point may not be the same for all bicubic surface patches that contain the point. If a large number of control points are defined for both the $\theta$ and $z$ parameters, and the canopy surface is not discontinuous, the normal of the point on the canopy surface is nearly approximated by the normal at the point on the centered bicubic surface patch. A better approximation is obtained from the average of the normal at the point on the overlapping bicubic surface patches that contain the point.

The distance across a canopy surface between two points on the surface is computed using an adaptive quadrature algorithm known in the art. The algorithm constructs a surface curve between the two points and subdivides the curve into four segments equally spaced in the parameters $\theta$ and $z$. The sum of the Euclidean distance between the two original endpoints of these four segments is compared to the Euclidean distance between the two original endpoints. If the difference is within an acceptable tolerance, the length of the surface curve segment is the Euclidean distance between the original endpoints. Otherwise, the length of the surface curve segment is the sum of the distances calculated by the algorithm applied to each of the four segments, in a recursive manner.

Points on an XY plane are projected onto the canopy surface from a known surface point given by the $\theta$ and $z$ parameters. The $(x,y)$ rectangular coordinate values on the plane are converted to polar coordinates. The angle determines a surface curve that results from intersecting the surface with a rotated plane that is perpendicular to the tangent plane at the given surface point. The radius is the distance along this surface curve from the given point to the projected point.

The projection algorithm rotates the XY plane about the X-axis so that the normal vector of the XY plane has the same z-component as the normal vector at the surface point (with no x-component). This plane is then rotated about the normal vector of the new Z-axis until the normal vector of the new XY plane coincides with the normal vector at the surface point, and the origin of this new XY plane is translated to the given surface point. The point on the original XY plane is transformed into a point on the tangent plane to the surface. The $\theta$ and $z$ values of this transformed point in cylindrical coordinates are used to obtain the projected point on the surface. The requested distance (radius of the point on XY plane in polar coordinates), is compared to the distance between this projected point and the given surface point. If the difference is within an acceptable tolerance, the projected point is successfully mapped to the surface. Otherwise, the algorithm is repeated where the projected point becomes the given surface point, and a new point on the XY plane is determined using the same angle and the difference between the compared distances. If the projection algorithm does not converge within a certain number of iterations, the surface point most recently used as the given surface point is accepted.

Image resolution requirements demand that the inspection system take relatively small (approximately 6×7 inch) images of the canopy surface during the initial overall inspection of the surface area, which can be up to 45 square feet. This requires a careful scheme for the control of where the center of each field of view (FOV) falls on the surface of the canopy. The canopy model is used to generate overlapping regions (sectors) of the proper FOV size and to provide a surface normal vector for inspection camera orientation.

Figure 3:
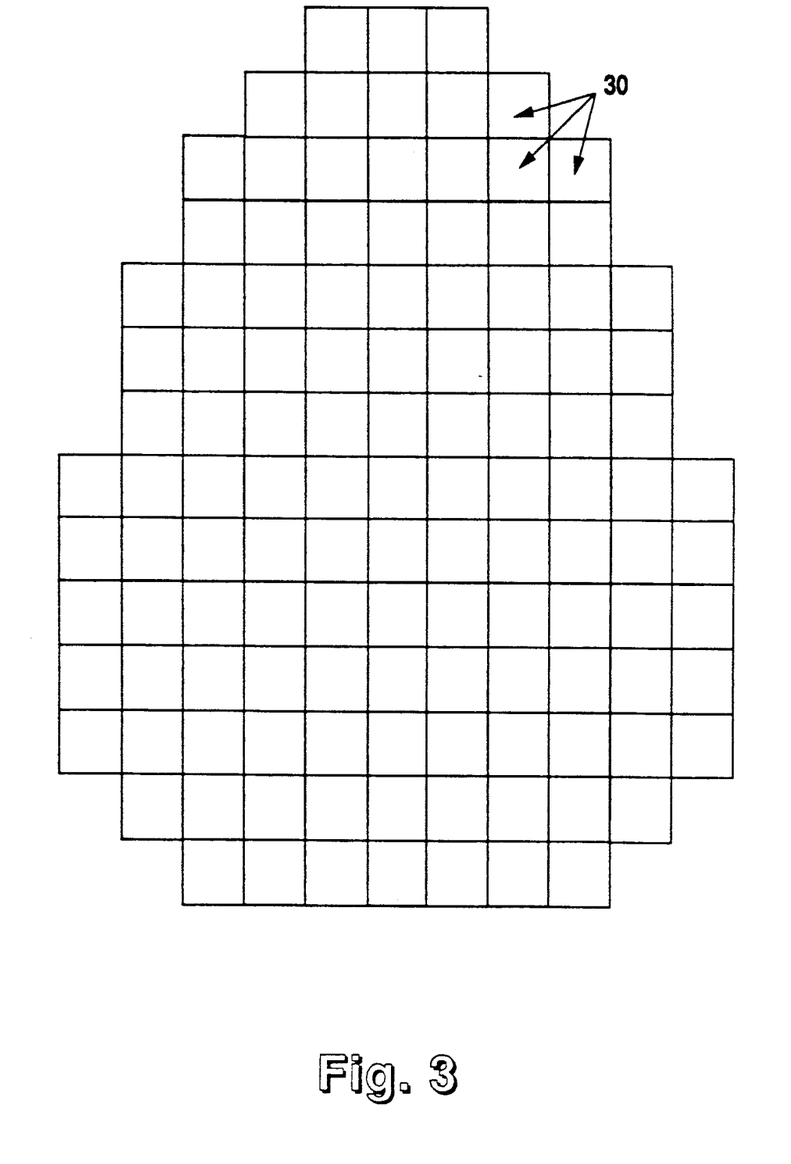
FIG. 3 is a graphical representation of a plurality of inspection sectors used to map a canopy such as that shown in FIG. 2.

FIG. 3 is an illustration of a sector map for a fighter canopy which has been subdivided into vision inspection sectors illustrated by reference numeral 30. (The sectors in the figure are not to scale, nor does the figure denote sector overlap). The entirety of the canopy's area of interest falls within the course boundary set out by the rectangular quantization of the inspection sectors.

Figure 4:
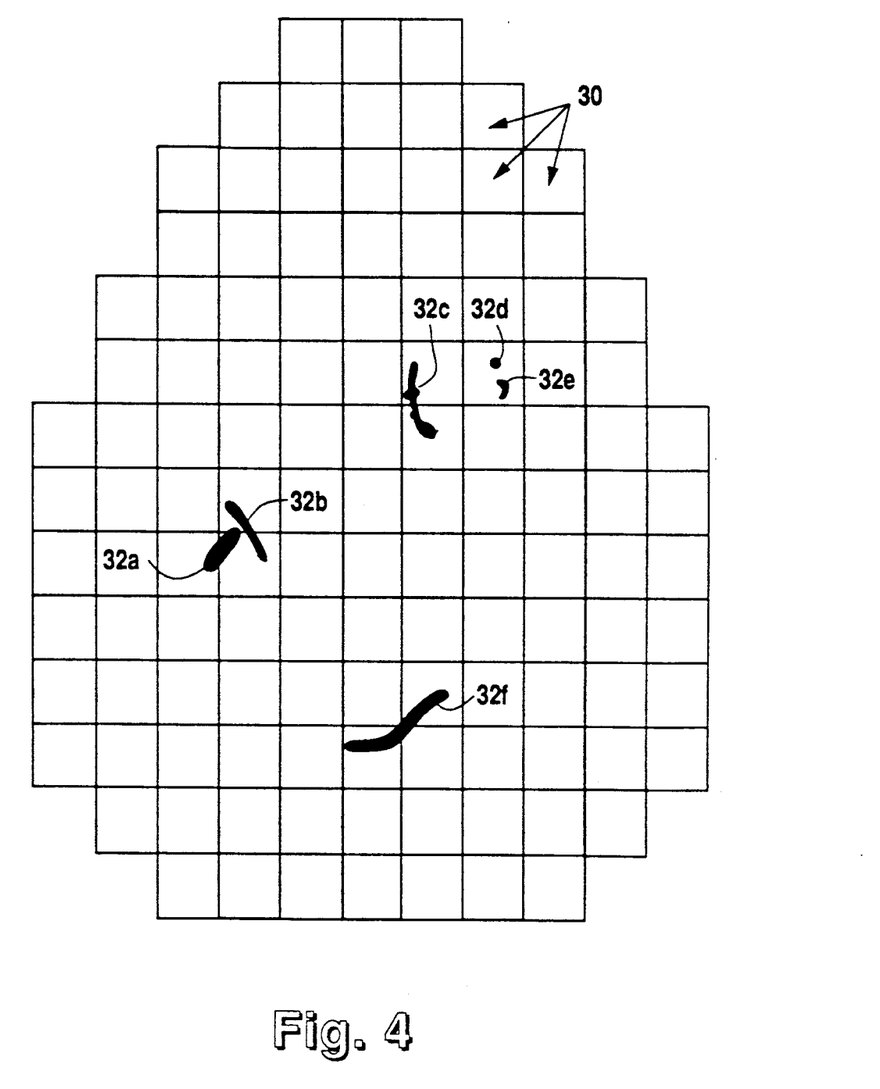
FIG. 4 is an illustration of a plurality of flaws mapped on the inspection sectors shown in FIG. 3.

In the first of identifying flaws, the transparency is prepared to allow inspection to determine the location of flaws. This is accomplished by covering both surfaces of the canopy with white, water soluble paint, which can be easily removed with light polishing of the surface. The light polishing will remove the paint from portions of the surface which do not contain flaws, but will leave paint in areas which contain flaws. The canopy is mapped using the above described imaging technique. The images are then analyzed for flaw information. General image processing techniques, known in the art, are used to abate noise and other artifacts. When both sides of the canopy have been cleaned, the marked areas are inspected again to determine the relative severity of the flaws. Flaw graduation occurs as the flaws are categorized as being either major or minor, where a major flaw would generally be more than 0.003 inches deep. The severity of the flaw is determined in the invention system by correlating the number of pixels corresponding to each flaw as measured by the output signal of the video camera 16. When processing is complete, a map is constructed (using techniques discussed below) for each flaw to provide information relating to its severity, shape, location, and on which surface it appears. FIG. 4 is an illustration of a sector map for a canopy showing a plurality of flaws 32a-32f mapped into various inspection sectors of the map.

PAD PRESSURE PROFILE

Figure 5:
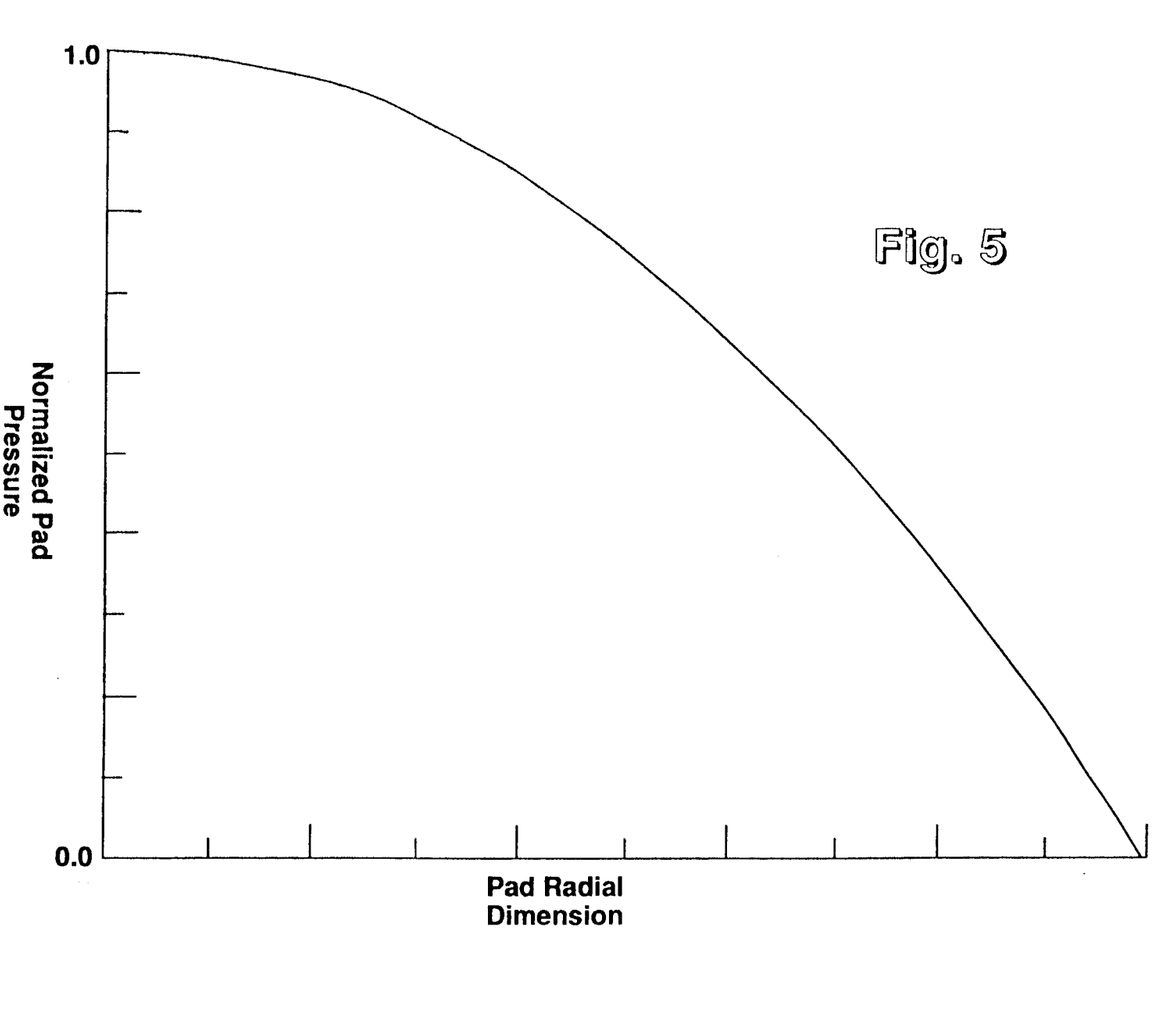
FIG. 5 is a graphical representation of pad pressure profile as a function of normalized pad pressure and pad radial dimension for grinding pads used in the polishing mechanism of the present invention.

When a sanding pad of the polishing mechanism 10 is in contact with the surface, the amount of pressure applied varies across the pad. The pad pressure profile is a function which yields the amount of pressure applied to the canopy surface at any point on the grinding end effector pad. FIG. 5 is a graphical illustration of the pad pressure profile for sanding pads on a polishing mechanism 10 of the type used in the present invention. The pad pressure profile is assumed to be radially symmetric and is modelled by a second order polynomial function of the radius.

The amount of material removed by the canopy grinding operation at a point on the canopy surface is proportional to the summation over time of the pad pressure profile function evaluated for that surface point under the grinding pad of the polisher 10 at each grinding path position. The amount of material removed about an area on the canopy surface for a grinding path is called the material removal pattern.

IDEAL MATERIAL REMOVAL PATTERN

For a finitely small flaw mark at a point on the surface of the canopy, the ideal material removal pattern is defined to be a circular pattern with the following constraints:

The amount of material removed is radially symmetric; i.e. strictly a function of the radius of the circular pattern.

The maximum amount of material is removed at the center of the pattern. The center of the pattern, i.e. the point where the pattern radius is zero, is positioned over the finitely small flaw mark. The maximum amount of material to remove here is the gauged depth of the flaw.

No material at the outer edge of the pattern is removed. The outer edge is defined by the set of points at the maximum radius of the pattern.

The slope of the material removal as a fraction of the pattern radius must be zero at the center of the pattern and at the edges of the pattern. This is to avoid any discontinuities in the ideal material removal pattern.

Material removal as a function of the pattern radius must be a smooth continuous function in order to minimize the distortion.

Figure 6:
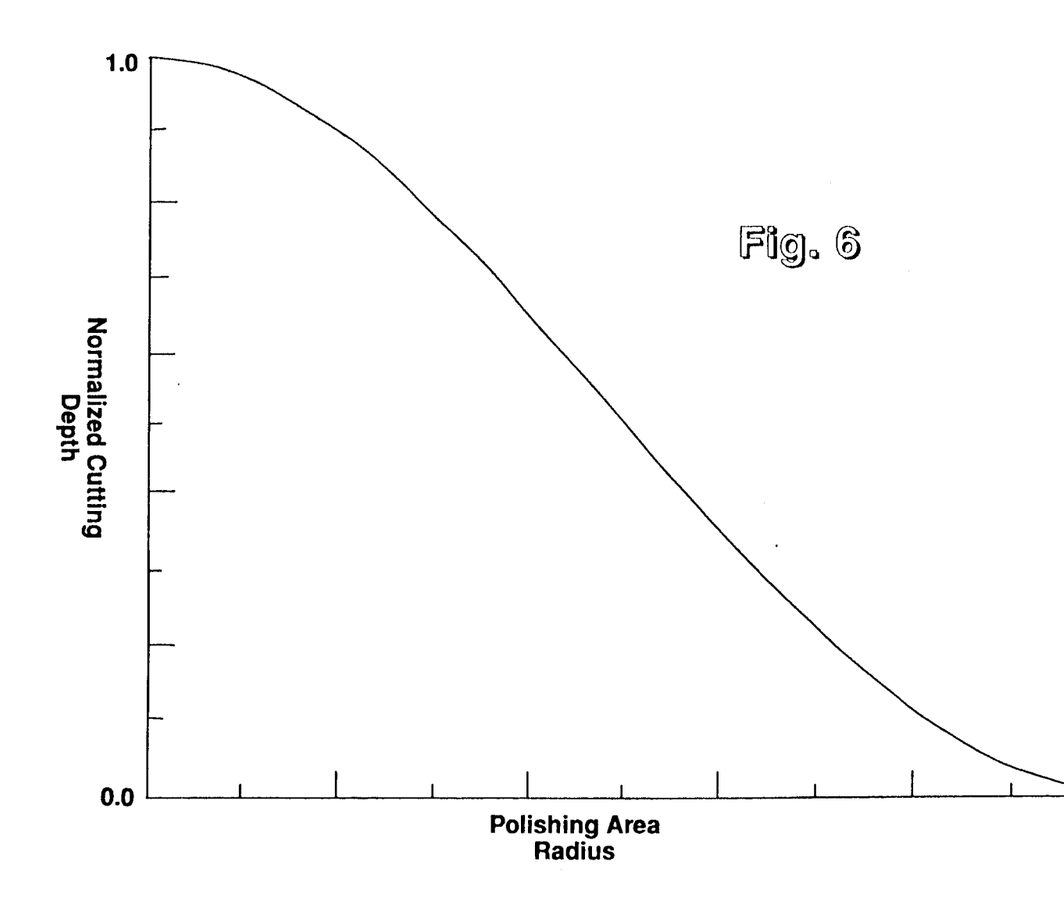
FIG. 6 is a graphical representation of an ideal material removal curve in terms of normalized cutting depth and polishing area radius.

FIG. 6 is a graphical illustration of the ideal material removal curve in terms of normalized cutting depth and polishing area radius. Note the curve has a zero slope at the point of intersection with the vertical axis and that the slope is also approximately zero as the right hand portion of the curve becomes asymtopic with the horizontal axis.

Under the above conditions, the material removal as a function of the pattern radius is represented by a cubic polynomial with the proper coefficients. Let $r_{max}$ be the maximum pattern radius where $r_{max} > 0$. Let r be any radius such that $0 \leq r \leq r_{max}$. Then the normalized radius $\hat{r}$ is defined by $$\hat{r} = r/r_{max}$$

Let h be the gauged depth of the flaw mark. Then the material removal as a function m(r) of the normalized radius is defined to be the parametric cubic curve given by $$m(\hat{r}) = h(a_3\hat{r}^3 + a_2\hat{r}^2 + a_1\hat{r} + a_0)$$

and the function $\dot{m}(\hat{r})$ which represents the slope of the curve is given by $$\dot{m}(\hat{r}) = h(3a_3\hat{r}^2 + 2a_2\hat{r} + a_1)$$

The constraints on the circular pattern as an ideal material removal pattern can be expressed in terms of the functions $m(\hat{r})$ and $\dot{m}(\hat{r})$, by $$m(0)=h=ha_0$$

$$m(1)=0=h(a_3+a_2+a_1+a_0)$$

$$\dot{m}(0)=0=h(a_1)$$

$$\dot{m}(1)=0=h(3a_3+2a_2+a_1)$$

Solving this set of four simultaneous equations for the four unknown coefficients yields $$\dot{m}(\hat{r})=h(2\hat{r}^3=3\hat{r}^2+1)$$

Figure 7:
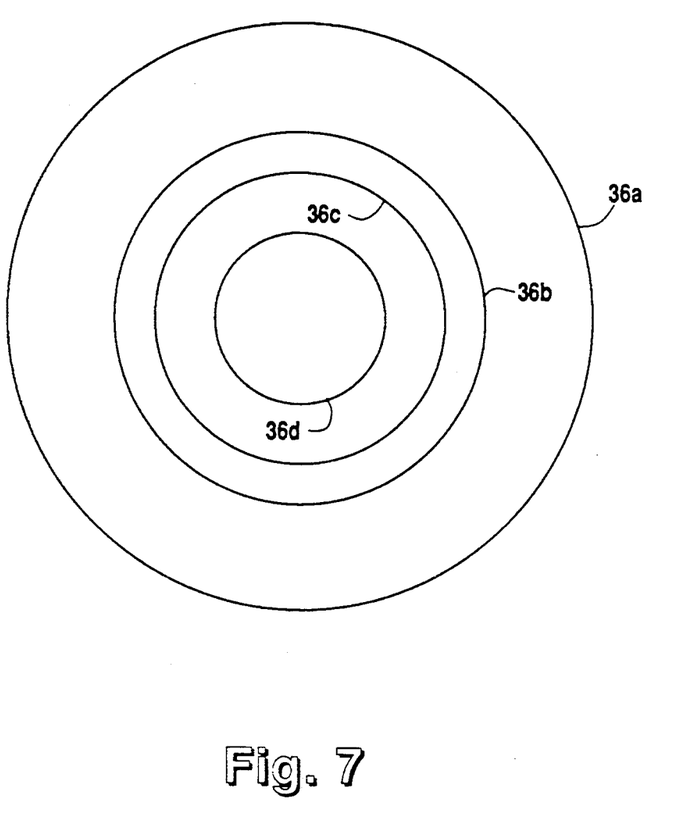
FIG. 7 is an illustration of a family of concentric circles representing possible grinding pads for the orbital polishing tool used in the present invention.

The robot grinding path for an idea material removal pattern, which is a circular pattern on the canopy of some specified maximum radius, is constructed from a series of concentric circular paths. FIG. 7 is an illustration of a family of concentric circles 36a-36d representing possible grinding paths. Each concentric path is controlled by two parameters: the radius of the path from the center of the pattern and a grinding coefficient which corresponds to the amount of time to be spent by the robot in following this path. The time for following a concentric circular path is a function of the commanded robot speed and the spacing between points along the path (empirically, while holding the commanded robot speed constant, the distance between tightly spaced points is a more accurate control for the actual robot velocity). A robot grinding path is constructed by matching the summation of material removal patterns for the concentric circular paths to the ideal material removal pattern by varying the two circular path parameters using methods of least squares.

Figure 8:
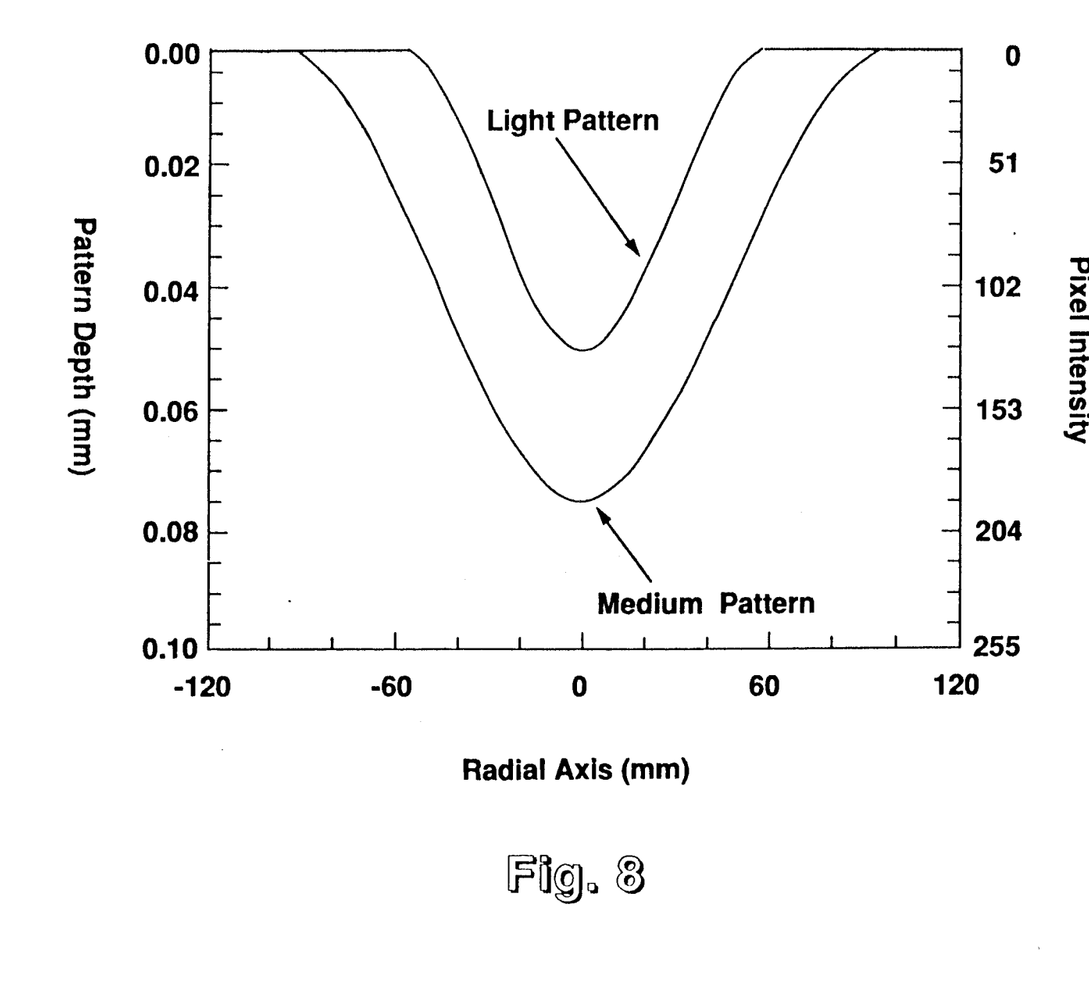
FIG. 8 is a graph of the radial cut of medium and light patterns used for grinding a canopy surface to remove flaws.

The gauging of flaw depths results in the classification of flaws into two severity groups: major and minor. From this classification, a single ideal material removal pattern is constructed for each severity group—a medium ideal pattern for major flaws and a light ideal pattern for minor flaws. To simplify nomenclature, the medium ideal pattern and the light ideal pattern will be referred to as the medium pattern and light pattern, respectively. The medium pattern removes material to 1.5 times the depth that the light pattern removes material, and the medium pattern removes material over 1.5 times the surface area as that for the light pattern. FIG. 8 is a graphical illustration of the amount of material removal along a radial cut of the medium and light patterns. The material removal curves are shown as a function of radial axis versus pattern depth and also as a function of radial axis versus pixel intensity.

A larger area flaw mark is considered as a closed collection of many of many finitely small flaw marks. For simplicity, the severity of the composite flaw mark is considered to be the average severity of each of these smaller flaw marks. The ideal material removal pattern for this composite flaw mark is constructed from the ideal material removal patterns for each of these smaller flaw marks. This is done by using the maximum amount of material removal at every finitely small point on the canopy surface from the superimposed ideal material removal patterns for each of these smaller flaw marks.

Consider such a composite flaw that has an arbitrary shape and size. For a very large composite flaw, it would be impossible to construct a robot grinding path which would guarantee that every point along the path could be reached with the robot polishing mechanism 10 being normal to the surface (this problem is due to the finite work envelop of a given robot). Furthermore, for an irregular flaw mark shape, the amount of numerical computation to construct the optimal robot grinding path would be overwhelming and it would be difficult to accurately determine the proper grinding coefficients. The ideal material removal pattern for the composite flaw can be more easily constructed by limiting robot grinding paths to be constructed only for the medium and light patterns, and by developing a strategy for optimal placement of these two patterns.

The placement of an ideal material removal pattern yields a robot grinding path which is mapped to the surface of the canopy. The canopy surface point at the center of this robot grinding path is called a grind site. This concept can be understood by considering a specific composite flaw mark that is long and linear. The medium pattern is selected if the flaw is major; otherwise, the light pattern is selected. The selected material removal pattern is centered in the middle of this linear flaw mark. The length of this linear sequence of flaw marks that is completely removed by the selected material removal pattern is called the effective cutting diameter for that material removal pattern. The effective cutting radius is half of this effective cutting diameter.

For the finitely small flaw, a circular pattern is constructed of the effective cutting radius for the medium pattern where the amount of material removed at every point inside the effective cutting radius is the amount of material removed at the effective cutting radius of the medium pattern. This circular pattern is called the medium effective cutting pattern. A similar pattern is constructed using the effective cutting radius of the light pattern. This circular pattern is called the light effective cutting pattern.

SUPERCLUSTERING

Clustering refers to the process of linking flaws together into groups because they will interact with one another during their removal. In superclustering, flaws may be drawn from any of the inspection sectors if they are considered proximal. In perfect superclustering, each point on a flaw is searched against every other point on every other flaw to determine if any of the points fall within a light or medium pattern radius of the reference point. A simple and faster method uses the bounding box of the flaws (the rectangular box formed by the maximum and minimum extensions of the flaw's outline on both of the coordinate axes) to determine the flaw extent.

The process begins by declaring the first flaw as the root of a supercluster. Subsequent flaws are then searched for proximity to the root or to the current members of the expanding supercluster. If such flaws are within the effective cutting radius of a medium pattern, they are appended to the cluster and the search restarts. This continues until no more additions to the cluster are made. The next unused flaw is the root of the next supercluster. The superclustering process is complete when all flaws are members of a cluster for both surfaces of the canopy.

For most superclusters, the next step of operation is the preparation for grind site location selection. Flaws from various inspection sectors are required to be gathered together into a single graphical image for processing. This effort is usually accurate, except for certain areas of the canopies where extensive curvature induces misalignment between the overlapping adjacent frames. This overlap is controlled so that it is possible to add reduced-scale flaw images together maintaining a 1:1 aspect ratio in scale (the scale factor is the same for both axes). The scale used for the reduction is determined by the maximum spread of the cluster across inspection sectors, but is not allowed to be less than two. This minimum scale factor allows the scaled medium pattern to fit within the image frame boundaries of the video inspection system, and is the prevalent scale factor observed during system operation.

Superclusters with only one element present a special case to the algorithm. If such a cluster can fit within the effective cutting radius for its stated severity, then it is possible to create a grind site immediately, using the centroid of the flaw as the grind site's center. If the flaw does not completely fit within the effective cutting radius, then it must be classed with the other, more complex forms of superclusters, i.e., those with multiple flaws and the possibility of multiple vision sector involvement.

Figure 9:
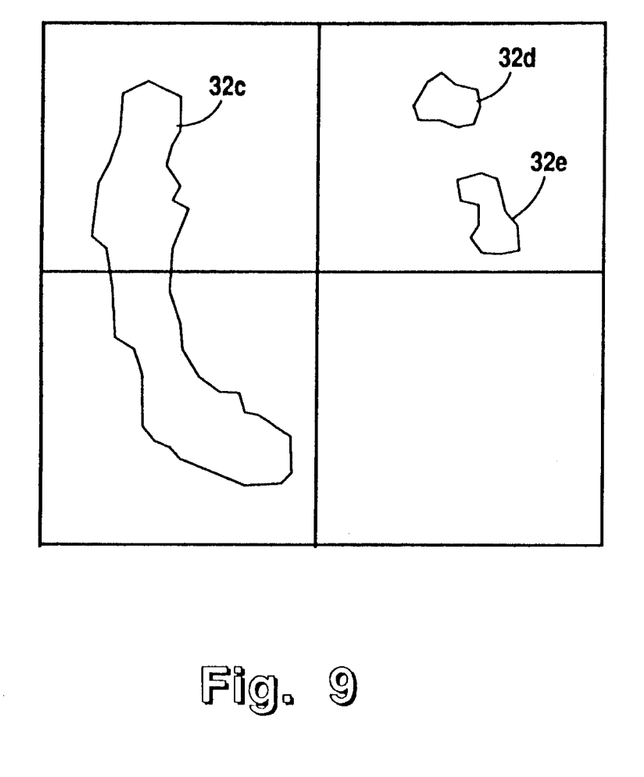
FIG. 9 is an enlarged view of a group of the flaws shown in FIG. 4.

FIG. 9 shows hypothetical flaw images corresponding to individual flaws 32c, 32d, and 32e of FIG. 4 following the superclustering operations. The large flaw 32c to the left of the image has been classified as a major flaw, while the two flaws 32d and 32e in the upper right of the image are minor. The composite flaw image generated is now ready for a simple process designed to create the boundaries for the search for grind site locations. In designing a set of boundaries, ideally, one would like a grinding pattern to fall somewhere on a flaw for maximum effectiveness. Alternatively, it may be possible to remove flaws with pattern centers placed not on the flaw, but near the flaw, such that the patterns' effective cutting radii sweep through multiple flaws.

In the present invention, the flaw severities are used to create a new image based upon effective cutting patterns. As was discussed above, the number of pixels recorded by the vision system can be correlated with the severity of the flaw. For each pixel in the image of a particular severity, an effective cutting pattern of that severity is placed in the output image. Referring again to FIG. 8, it can be seen that the effective cutting depth can be correlated with a number of pixels forming an image. Further, grey-level representations of effective pattern can also be created in terms of grey level figures comprised of a plurality of pixels. Each severity estimate is done separately as a binary operation, then brought together with the proper identifying grey-level representation in the final image, which is the effective cutting area image shown in FIG. 10. The reference numeral 40 corresponds to the effective cutting area image for flaw 32c, while the reference numeral 42 corresponds to the effective cutting area image for flaws 32d and 32e. In this figure, grey scales are not shown; however, in practice minor flaws merged with light patterns will be assigned a grey-level darker than that of major flaws merged with medium patterns. Note that the two light flaws 32d and 32e in the upper right-hand corner of the image have been merged into a larger pattern image 42 in FIG. 10. This feature is very desirable to minimize the number of grinding sites selected. The images 40 and 42 are now ready to be searched to determine the location of grinding sites.

TEMPLATE MATCHING

The optimal selection of grinding sites involves efficiently matching combinations of the medium and light pattern images to the effective cutting area image. In many image analysis applications, it is necessary to determine whether an image contains a particular object, and, if present, the exact location of that object. Provided that the appearance of this feature in the image is known accurately, then object detection can be performed by a template matching operation where the object searched for is the template that is compared to the image under investigation. A variety of measures of match or mismatch are used in template matching algorithms, as can be found in the following references: A. Rosenfield and A. C. Kak, *Digital Picture Processing*, 2nd Edition, Vols. 1 and 2, Academic Press, 1982; and G. X. Ritter, J. N. Wilson and J. L. Davidson, *Image Algebra: An Overview*, Internal Report, University of Florida, Center for Computer Vision Research, July 1988.

The grind site selection strategy employs a template matching technique which is based on a unified and algebraic approach to image processing. The following is a brief discussion of a framework for using template matching.

Let the set of integers Z be a value set, and let $X = (Z_N \times Z_N)$ be a two-dimensional coordinate set of the non-negative integers 0, 1, . . . , N−1. Then a Z valued image A on coordinate set X is a graph of the function $A: X \rightarrow Z$ and is given by $$A = \{(x, A(x)) : x \in X, A(x) \in Z\}.$$

In this notion, an element $(x, A(x))$ in the image A is called a picture element or pixel, where x is the pixel location, and $A(x)$ is the pixel value. The set of all Z valued images on X is denoted $Z^X$.

Let A and B be two images in $Z^X$. Then addition, multiplication, and maximum are defined by:

$$A + B = \{(x, C(x)) : C(x) = A(x) + B(x), x \in X\},$$

$$AB = \{(x, C(x)) : C(x) = A(x)B(x), x \in X\},$$

$$\max(A, B) = \{(x, C(x)) : C(x) = \max(A(x), B(x)), x \in X\}.$$

An image $C \in Z^X$ is called a constant image if all its grey values are the same; i.e. $C(x) = k$ for all $x \in X$ and for some $k \in Z$. Then $kA = CA$ and $k + A = C + A$. If $C(x) = 0$ for all $x \in X$, then $C = 0$ is the constant zero image; if $C(x) = 1$ for all $x \in X$, then $C = 1$ is the constant unit image. For image A and B, the operations of subtraction and minimum can be expressed by $$A - B = A + ((-1)B) = A + (-B),$$

$$\min(A, B) = -\max(-A, -B).$$

Let $X = (Z_N \times Z_N)$ be a two dimensional N×N coordinate set and let $Y \subseteq (Z_N \times Z_N)$ be a subset of a two dimensional coordinate set. Then a generalized Z valued template t from Y to X is a function $t: Y \rightarrow X$. For each $y \in Y$, template $t_y \in Z^X$ is a Z valued image on X, and is given by $$t_y = \{(x, t_y(x)) : x \in X\}$$

The template $t_y$ depends on the target pixel y and the template weights $t_y(x)$. Let $(Z^X)^Y$ denote the set of all Z valued templates from Y to X. The configuration of a template $t_y \epsilon (Z^X)^Y$ which represents a medium or light pattern is given by $$S(t_y) = \{((x_1+r+N)\bmod N, (x_2+c+N)\bmod N) \epsilon X\}$$

under the conditions that $x_1, x_2 \epsilon Z_N$, such that $(x_1, x_2) \epsilon X$ is the center of the template;

$(-N/2) < r, c < (N/2)$, for $r, c \epsilon Z$ (row and column indices);

$(r^2+c^2)^{\frac{1}{2}} < r_{max}$, where $r_{max}$ is the maximum radius of the medium or light pattern;

$t_y((x_1+r+N)\bmod N, (x_2+c+N)\bmod N)$ is given by $m(\hat{r})$, the material removal as a function of the normalized radius;

$\hat{r} = (r^2+c^2)^{\frac{1}{2}}/r_{max}$

Let $A \epsilon Z^X$ be the effective cutting area image and $B \epsilon Z^Y$ be an image to store the results of a template matching operation. Let $t_y \epsilon (Z^X)^Y$ be a template with configuration $S(t_y)$ given above. Define the absolute difference template mismatch operation by $$A \sim t = \{(y, B(y)) : B(y) = \Sigma |A(x) - t_y(x)|, y \epsilon Y\} \times \epsilon S(t_y)$$

The image $B = A \sim t$ contains the mismatch value y when the template $t_y$ was centered over the pixel in image A at coordinate x. The minimum mismatch value is given in image B by an $y \epsilon Y$, where $B(y) \leq B(y)$ for all $y \epsilon Y$.

This corresponds to the best placement of the medium or light pattern in image A at coordinate x. The operation of removing this best matched medium or light pattern is expressed by $\max(0, (A - t_y))$. The coordinate set $Y \subseteq (Z_N \times Z_N)$ is given by $$Y = \{y = x \epsilon X : 0 < A(x) \leq c\}$$

where the constant c is the grey value of the medium or light effective cutting pattern. This implies that the only locations a template match will be attempted is at pixels in the effective cutting area image A with pixel values exceeding the pixel value of an effective cutting pattern.

The template matching calculations can be visualized by imagining the template being shifted across the image to different offsets, where the template is a gray level representation of the medium or light pattern. The template is shifted to offsets in the image such that the center of the template is positioned over a point on the image with a positive gray value greater than or equal to that of the effective cutting pattern. When the template is shifted to an offset that is near the boundary of an image, the template shift is allowed to wrap around in the image instead of being clipped at the boundary. The sum of the absolute differences between the superimposed gray values within the area of the template is computed, and the offset where a minimum sum occurs is the location of the best match.

Alternatively, the template matching calculations can be visualized by imaging the template in the center of some image, and the source image being shifted across the template image by different offsets. The source image is shifted by offsets to the center of the template image, where the offsets are determined by every point on the source image with a positive grey value greater than or equal to that of the effective cutting pattern. When the source image is shifted by an offset determined by a point near the boundary of an image, the source image shift is allowed to wrap around. The template image has a corresponding mask image which contains a gray value of one for every non-zero gray value in the template image. The sum of the absolute differences between the superimposed gray value within the area of the template, is computed from the dot product of the mask image with the image from the absolute difference of the template image with the shifted source image.

Figure 10:
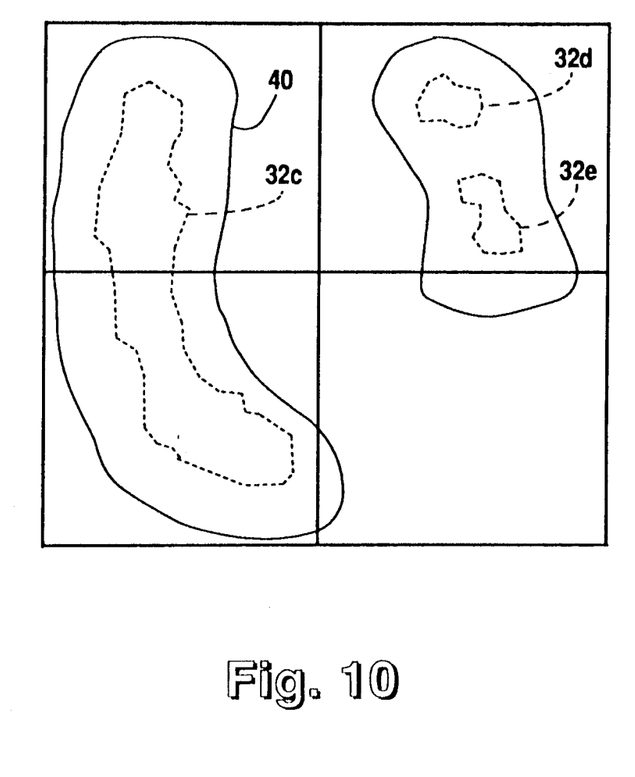
FIG. 10 is an illustration of the effective cutting area image for the flaws shown in FIG. 9.

Given a flaw image that has been mapped into an effective cutting area image such as those shown in FIG. 10, the system determines grind sites by placing ideal patterns, where the medium patterns are to be placed first. The grey-level representations of the light and medium patterns can be determined by the pixel density scale shown in FIG. 8. It is generally preferable to place a larger pattern once, than to place a smaller pattern several times. This stems largely from concerns for minimizing the optical distortion in the canopy. Pattern overlap deep into the effective cutting radius from placing multiple adjacent patterns can produce unusual artifacts in the plastic. A medium pattern can be used on a light flaw area, or on residual medium material (material near a grind site that has not been completely removed).

The medium pattern is the template used in the absolute-difference template mismatch technique and measures of pattern fit are generated to determine the best position in the image for the pattern. The location in the image with the lowest mismatch is selected by the algorithm. Suitability of this location is determined by the use of thresholds. A threshold exists for both the light and medium patterns, and is defined to be quality of mismatch where a perfect mismatch for a given severity is the volume described by the ideal pattern of that severity. The volume of that pattern is the sum of the difference of that pattern taken against a black background, which would be an area without flaw information. Fractions of the perfect value are calculated and used to control when to accept a decision to place a pattern.

Figure 11:
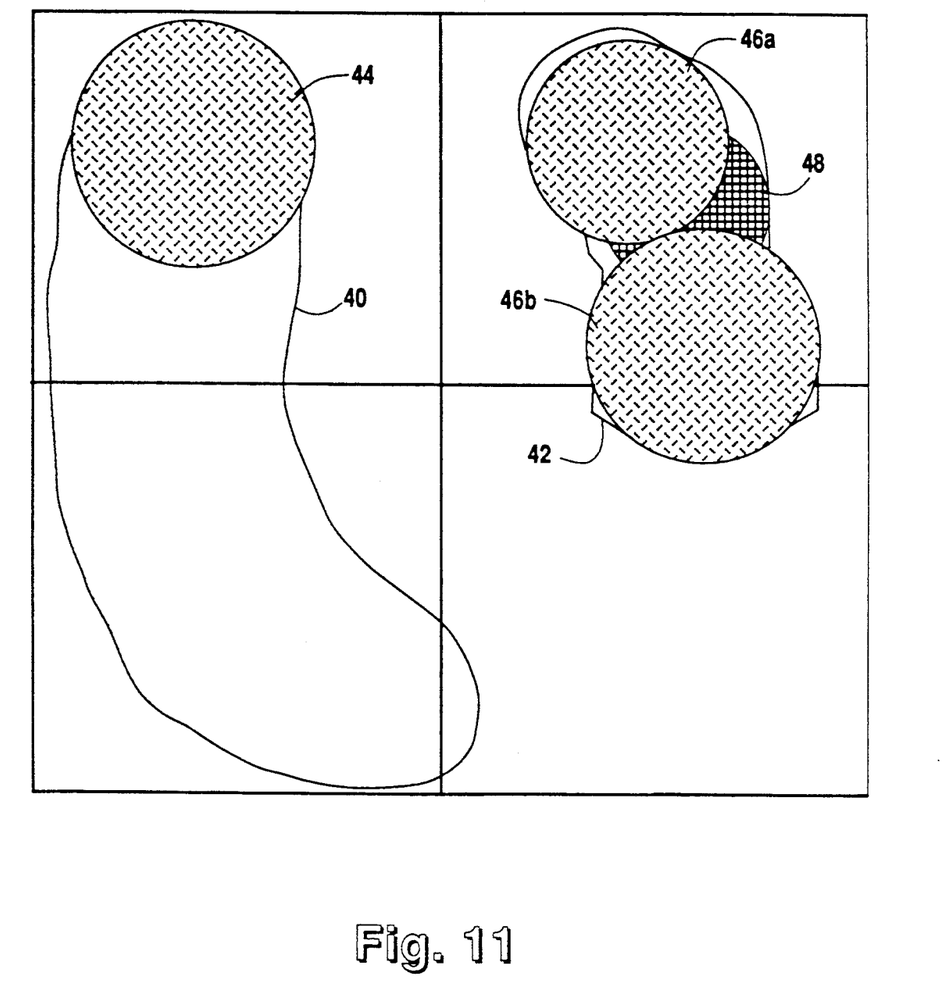
FIG. 11 is an illustration of a plurality of grinding patterns placed within the cutting area image of FIG. 10 using the template matching technique of the present invention.

After the algorithm selects the first tentative grind site, and the mismatch has satisfied the threshold criterion, the pattern may be placed. Placing the pattern entails removing that pattern from further consideration by subtraction. The process repeats, attempting to place medium patterns until no medium pattern can be placed within the mismatched criterion, and then attempts to place light patterns. Two primary methods are used to control the operation of the grind site selection algorithm: mismatch threshold, and the effective cutting radius. The mismatch thresholds are very critical values and have been empirically refined over time to produce repeatable quality results. The thresholds must be set to minimize unnecessary patterns, and yet to remove all of the flaws. The effective cutting radius controls how closely each type of pattern can be placed on the canopy. This number is closely related to changes in the grinding operation. While the numbers used initially for these values were based on system tests specifically designed to determine them, exhaustive operations revealed that these numbers could be altered to produce better results. Patterns can be separated to moved together at will for each severity to match the demonstrated grinding results. FIG. 11 shows a plurality of grinding patterns which have been fitted to the grinding patterns shown in FIG. 10. The grinding patterns are shaded to illustrate light and medium patterns. Grinding pattern 44 represents a light pattern which has been placed at one end of the grinding path to remove the flaw 32c shown in FIGS. 9 and 10. Subsequent grinding patterns can be added, in accordance with the template matching technique discussed above, to completely fill the grinding pattern thereby removing the flaw. The smaller flaws 32d and 32e, shown in FIGS. 9 and 10, have been removed by grinding patterns 46a, 46b and 48. Grinding patterns 46a and 46b are both medium grinding patterns having approximately the same diameter. Pattern 48 is a light grinding pattern having a slightly smaller diameter than the two medium patterns. The aggregate material removal resulting from the combined grinding patterns will result in the complete removal of flaws 32d and 32e shown in FIGS. 9 and 10.

Although the method and apparatus of the present invention has been described in connection with the preferred embodiment, it is not intended to be limited to the specific form set forth herein, but on the contrary, it is intended to cover such modifications, alternatives and equivalents as can reasonably be included within the spirit and scope of the claims.

What is claimed is:

1. A system for removing flaws from the surface of a material, such as a transparent aircraft canopy, comprising:
    a canopy;
    means for obtaining a video signal representation of the surface of said canopy, wherein said means for obtaining a video signal representation of said canopy comprises means for mapping said surface of said canopy to obtain a plurality of mapped sectors, the location of said flaws being correlated with the location of said mapped sectors;
    means for processing said video signal representation of said surface of said canopy to locate flaws in said surface;
    means for determining an optimal grinding pattern for removing said flaws from said canopy; and
    means for polishing the surface of said canopy in accordance with said grinding pattern to remove said flaws from said surface.

2. The system according to claim 1, said means for determining said optimal grinding pattern further comprising means for calculating an optimum pad pressure profile, said pad pressure profile being correlated, in accordance with said optimal grinding pattern, with the amount of material to be removed from the surface of said canopy by a grinding pad on said polishing means.

3. The system according to claim 2, wherein said pad pressure profile is determined by a second order polynomial as a function of the radius of a polishing pad.

4. The system according to claim 3, wherein said flaws are grouped in clusters to minimize the number of grinding patterns needed to remove said flaws.

5. The system according to claim 4, wherein said optimum grinding pattern is a cubic polynomial function of the radius of said polishing pad.

6. The system according to claim 5, wherein said flaws are removed by grinding a plurality of circular patterns in said surface of said canopy in accordance with said optimum grinding pattern.

7. A method of removing flaws from the surface of a material, such as transparent material used in an aircraft canopy, comprising the steps of:
    obtaining a video signal representation of the surface of a canopy;
    processing said video signal representation of said surface of said canopy to locate flaws in said surface;
    calculating an optimal grinding pattern for removing said flaws from said canopy;
    calculating a pad pressure profile, said pad pressure profile being correlated, in accordance with said optimal grinding pattern, with the amount of material to be removed from the surface of said canopy by a grinding pad on a polishing means; and polishing the surface of said canopy in accordance with said grinding pattern to remove said flaws from said surface.

8. The method according to claim 7, wherein said pad pressure profile is a second order polynomial function of the radius of said grinding pad.

9. The method according to claim 8, wherein said flaws are grouped in clusters to minimize the number of grinding patterns needed to remove said flaws.

10. The method according to claim 9, wherein said optimum grinding pattern is a cubic polynomial function of the radius of said grinding pad.

11. The system according to claim 10, wherein said step of polishing the surface of said canopy comprises the step of grinding a plurality of circular patterns in said surface of said canopy in accordance with said optimum grinding pattern.

* * * * *